US00PP16991P2

(12) United States Plant Patent
Olesen

(10) Patent No.: US PP16,991 P2
(45) Date of Patent: Aug. 15, 2006

(54) VARIETY DENOMINATION 'POULCAS018'

(50) Latin Name: ***Rosa* hybrid**
Varietal Denomination: Poulcas018

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 49 days.

(21) Appl. No.: 11/090,136

(22) Filed: Mar. 24, 2005

(51) Int. Cl.
*A01H 5/00* (2006.01)

(52) U.S. Cl. ..... Plt./145
(58) Field of Classification Search ..... Plt./145
See application file for complete search history.

*Primary Examiner*—Kent Bell
*Assistant Examiner*—Annette H Para

(57) ABSTRACT

A new garden rose plant of the floribunda class which has abundant, light yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas018'.

SUMMARY OF THE INVENTION

The present invention constitutes a new and distinct variety of garden rose plant which originated from a controlled crossing between the female seed parent, an unnamed seedling and the male pollen parent 'Poulsyng', U.S. Plant patent application Ser. No. 09/268,299 (abandoned).

The two parents were crossed during the summer of 1996 and the resulting seeds were planted in a controlled environment in Fredensborg, Denmark. The new variety, named 'Poulcas018', originated as a single seedling from the stated cross.

The new variety may be distinguished from its female seed parent by the following combination of characteristics:

1. The seed parent has fewer petals than 'Poulcas018'.
2. The seed parent has white flowers, while 'Poulcas018' has light yellow flowers.

The new variety may be distinguished from its male pollen parent by the following combination of characteristics:

1. The pollen parent has 34 to 40 petals. 'Poulcas018' has 130 petals.
2. Flowers of the pollen parent have a general tonality of Red Group 36A, while flowers of 'Poulcas018' are Yellow Group 4D to 4C.

The objective of the hybridization of this rose variety was to create a new and distinct variety for garden use with unique qualities, such as:

1. Uniform and abundant light yellow flowers with many petals;
2. Vigorous, but compact growth when propagated both as a budded rose and on its own roots;
3. Exceptional disease resistance;
4. Fragrant flowers.

This combination of qualities is not present in previously available commercial cultivars of this type, known to the inventors, and distinguish 'Poulcas018' from all other varieties of which we are aware.

As part of the rose development program, Mogens N. Olesen germinated the seeds from the aforementioned hybridization during winter of 1996 and conducted evaluations on the resulting seedlings in a controlled environment in Fredensborg, Denmark. 'Poulcas018' was selected in the spring of 1997 by the inventor as a single plant from the progeny of the aforementioned hybridization.

Asexual reproduction of 'Poulcas018' by traditional budding and rooted cuttings was first done by Mogens N. Olesen in the nursery in Fredensborg, Denmark in July, 1997. This initial and other subsequent asexual propagations conducted in controlled environments have demonstrated that the characteristics of 'Poulcas018' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcas018'. Specifically illustrated in the drawing are:

FIG. 1.1; Cluster of open flowers and flower buds, showing branching, and the attachment of leaves, buds, and pedicels;

FIG. 1.2; Open flower;

FIG. 1.3; Sepals, pedicel and reproductive flower parts;

FIG. 2.1; Flower petals, detached;

FIG. 2.2; Leaves;

FIG. 2.3; Mature and juvenile bare stems showing thorns.

DETAILED DESCRIPTION OF THE VARIETY

The following is a description of 'Poulcas018', as observed in its growth in a field nursery in Jackson County, Oreg. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulcs012', U.S. Plant Pat. No. 16,143 are compared to 'Poulcas018' in Chart 1.

CHART 1

| | 'Poulcas018' | 'Poulcs012' |
|---|---|---|
| Petal Count | 130 petals | 30 to 35 petals |
| Flower Diameter | 50 mm | 53 mm |
| Genaral Tonality of Flower Color | Yellow 4D with intonations of Yellow 4C | Yellow 4D |

FLOWER AND FLOWER BUD

Blooming habit: Continuous.

Flower bud:

*Size.*—Upon opening, 21 mm in length from base of receptacle to end of bud. Bud diameter is 15 mm.

*Bud form.*—Urceolate.

*Bud color.*—As sepals unfold, petals are Yellow-Green Group 154D to Green-Yellow Group 1C.

*Sepal inner surface.*—Color: Yellow-Green Group 145A with anthocyanic intonations of Greyed-Red Group 179A and Greyed-Orange Group 177A. Surface: Strongly pubescent.

*Sepal outer surface.*—Color: Yellow-Green Group 144A. Anthocyanic pigments the color of Greyed-Red Group 178A observed. Texture: Somewhat rough, with numerous stipitate glands.

*Sepal shape.*—Apex: Cirrhose. Base: Flat at union with receptacle.

*Sepal margin.*—Margins have strong foliaceous appendages on three of the five sepals.

*Sepal size.*—28 mm long by 10 mm wide.

*Receptacle.*—Texture: Smooth. Shape: Funnel-shaped. Size: 7 mm in height by 8 mm wide. Color: Yellow-Green Group 144A.

*Peduncle.*—Length: 40 to 50 mm. Diameter: 4 to 5 mm on average. Color: Yellow-Green Group 144A.

*Pedicel.*—Surface: Smooth. Length: 25 to 30 mm. Diameter: 3 mm on average. Color: Yellow-Green Group 144A with anthocyanic intonations of Greyed-Orange Group 177B. Strength: Strong.

Flower bud development: Flower buds are normally borne in clusters of 7 to 11 flower buds per stem. Occasionally, solitary flower buds develop on a flowering stem.

Flower bloom:

*Fragrance.*—Strong. Flowers have a fresh, perfume like fragrance.

*Duration.*—The blooms have a duration on the plant of approximately 8 to 10 days. Petals fall cleanly away from plant after flowers have fully matured.

*Size.*—Flower diameter is normally 50 mm when open. Flower depth is 30 to 35 mm.

*Flower shape.*—Flowers are initially calathiform with petals packed tightly into sections. As the flower matures, the upper portion becomes increasingly convex in form.

*Shape of flower, side view.*—Upon opening the upper portion is convex. The lower portion is flat. After opening, the upper portion is convex. The lower portion is concave.

Petalage: Flowers have 130 petals on average.

Petal color:

*Upon opening, outer petals.*—Upper surface: Yellow Group 4C to 4D. Lower surface: Yellow Group 4D.

*Upon opening, inner petals.*—Upper surface: Yellow Group 4C. Lower surface: Yellow Group 4C.

*Basal petal spots, upon opening.*—Upper surface: Yellow Group 4A. Lower surface: Yellow Group 4A.

*After opening, outer petals.*—Upper surface: Yellow Group 4D. Lower surface: Yellow Group 4D.

*After opening, inner petals.*—Upper surface: Yellow Group 4D. Lower surface: Yellow Group 4D.

*Basal petal spots, after opening.*—No distinctive coloration at the petal base observed.

General tonality: On open flower Yellow Group 4D with intonations of 4C. No change in the general tonality at the end of the 7th day.

Petals:

*Petal reflex.*—Somewhat reflexed.

*Margin.*—Entire and uniform.

*Shape.*—Variable. Inner petals are linear to elliptic. Their petal bases and apecies are acute. Outer, larger petals are broad elliptic with rounded apecies and bases shapes.

*Size.*—Outermost petals are 35×35 mm. Innermost petals are 20 mm long by 10 mm wide.

*Texture.*—Smooth.

*Thickness.*—Average to thin.

Petaloids: None observed.

Reproductive flower parts:

*Pollen.*—None observed.

*Anthers.*—Size: 3 mm in length. Color: Yellow Group13 B. Quantity: 15 to 20.

*Filaments.*—Color: Yellow Group 10 B. Length: 4 mm.

*Pistils.*—Length: 5 to 7 mm. Quantity: 55 to 60.

*Stigmas.*—Superior in location relative to the length of the filaments and the height of the anthers. Color: Yellow Group 7 A.

*Styles.*—Color: Red-Purple Group 61B. At the base of the style, color is Yellow-Green Group 149D.

*Hips.*—None Observed in the field nursery in Jackson County Oreg.

PLANT

Plant growth: Moderate, upright to bushy. When grown as a budded field grown plant on *Rosa multiflora* understock, the average height of the plant is 60 to 100 cm and the average width is 60 to 80 cm.

Stems:

*Color.*—Mature growth is Yellow-Green Group 144A.

*Length.*—On average, canes are 50 to 60 cm from the base of the plant to the flowering portion.

*Diameter.*—Normally 11 mm.

*Internodes.*—On mature canes, there is an average distance of 50 mm between nodes.

*Surface texture.*—Young wood: Smooth. Older wood: Smooth.

Thorns:

*Incidence.*—12 thorns per 10 cm of stem.

*Size.*—Average length of thorns on mature stems is 10 mm.

*Shape.*—Upper portion is flat. Lower portion is concave.

*Color.*—Juvenile thorns: Yellow-Green Group 145A with intonations of Greyed-Red Group 182A to 182B. Mature thorns: Greyed-Orange Group 167D and Greyed-Orange Group 165A.

Plant foliage: Normal number of leaflets leaves in middle of the stem: 5 leaflets.

*Compound leaf.*—145 mm (l)×100 (w).

*Quantity.*—2 leaves per 10 cm of stem on average.

*Color of mature foliage*.—Upper side: Yellow-Green Group 147A. Lower side: Yellow-Green Group 146B.

*Color of juvenile foliage*.—Upper side: Yellow-Green Group 144A with marginal intonations of Greyed-Purple Group 184A. Lower side: Yellow-Green Group 146C with generalized light anthocyanic intonations of Greyed-Purple Group 184B.

Plant leaves and leaflets:

*Stipules*.—Size: 30 mm in length on average. Quantity: 2 per compound leaf. Shape: Linear, slightly broad based with outward extending apecies. Margins: Finely serrated with few stipitate glands. Color: Yellow-Green Group 144A.

*Petiole*.—Length: 25 to 45 mm. Diameter: 2 mm.

*Petiole upper surface*.—Color: Greyed-Yellow Group 162C with light anthocyanic intonations of Greyed-Purple Group 185C. Observations: Few stipitate glands.

*Petiole lower surface*.—Color: Yellow-Green Group 145A. Observations: Smooth.

*Rachis*.—Length: 40 mm.

*Rachis upper surface*.—Color: Yellow-Green Group 144A with light intonations of Greyed-Purple Group 185 C. Observations: Stipitate glands observed.

*Rachis lower surface*.—Color: Yellow-Green Group 145A. Observations: Smooth with small prickles.

*Leaflet*.—Edge: Serrated. Size: Average size of the terminal leaflet on normal leaves is 59 mm in length by 39 mm wide. Shape: Generally elliptical. Base: Obtuse. Apex: Cuspidate. Texture: Smooth. Thickness: Thick. Arrangement: Odd pinnate. Venation: Reticulate. Glossiness: Glossy.

Disease resistance: Above average resistance to mildew, rust, black spot, and *Botrytis* under normal growing conditions in Jackson County, Oreg.

Cold hardiness: The variety is tolerant to USDA Cold Hardiness Zone 6.

Heat tolerance: The variety has been found to be suitable for climate conditions found in the American Horticulture Society heat zone 7.

It is claimed:

1. A new and distinct variety of rose plant of the floribunda rose class named 'Poulcas018', illustrated and described herein, due to its abundant, light yellow, fragrant flowers, disease resistance, and extended period of bloom.

* * * * *

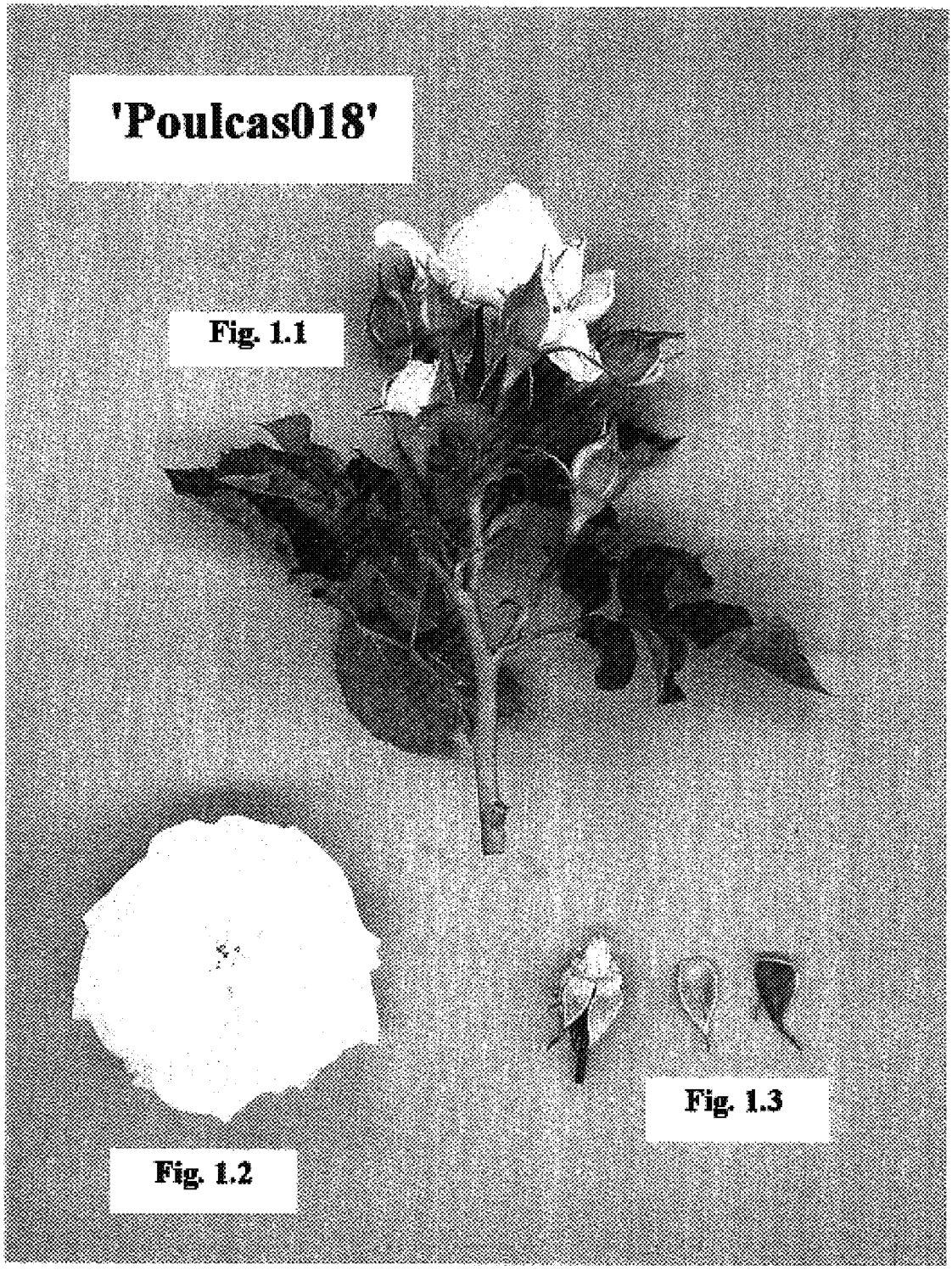
'Poulcas018'
Fig. 1.1
Fig. 1.2
Fig. 1.3

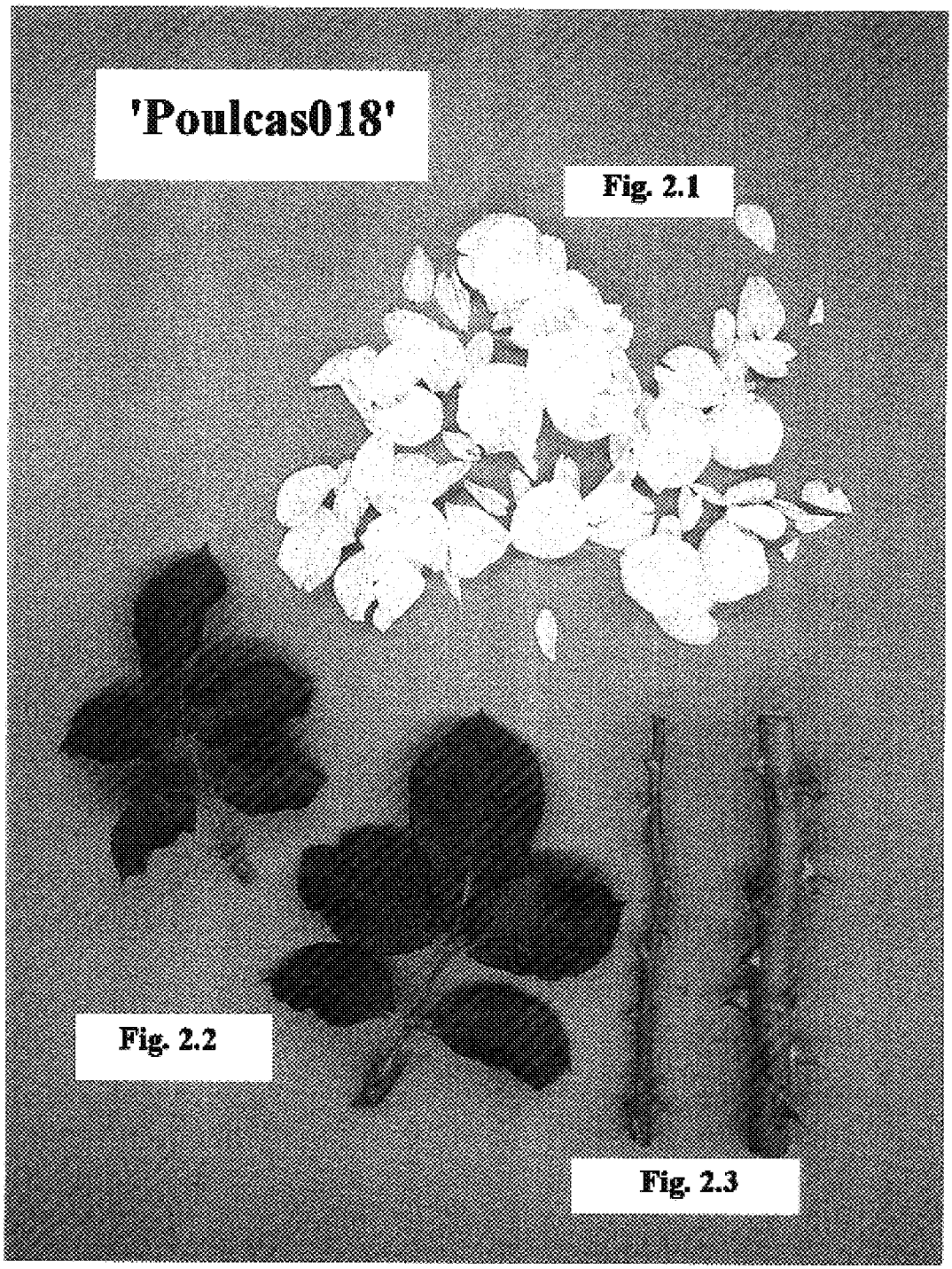
'Poulcas018'
Fig. 2.1
Fig. 2.2
Fig. 2.3